(12) United States Patent
Fukuda

(10) Patent No.: US 10,687,747 B2
(45) Date of Patent: Jun. 23, 2020

(54) MEDICAL NEEDLE AND PUNCTURE TOOL

(71) Applicant: Lightnix, Inc., Nishinomiya-shi, Hyogo (JP)

(72) Inventor: Mitsuo Fukuda, Hyogo (JP)

(73) Assignee: Lightnix, Inc., Nishinomiya-shi (JP)

( * ) Notice: Subject to any disclaimer, the term of this patent is extended or adjusted under 35 U.S.C. 154(b) by 116 days.

(21) Appl. No.: 15/116,975

(22) PCT Filed: Feb. 4, 2015

(86) PCT No.: PCT/JP2015/053027
§ 371 (c)(1),
(2) Date: Aug. 5, 2016

(87) PCT Pub. No.: WO2015/122323
PCT Pub. Date: Aug. 20, 2015

(65) Prior Publication Data
US 2017/0188924 A1     Jul. 6, 2017

(30) Foreign Application Priority Data
Feb. 14, 2014  (JP) .................................. 2014-026564

(51) Int. Cl.
 *A61B 5/15*     (2006.01)
 *A61B 5/151*    (2006.01)
 *A61B 10/02*    (2006.01)

(52) U.S. Cl.
 CPC ................ *A61B 5/15* (2013.01); *A61B 5/151* (2013.01); *A61B 5/1519* (2013.01);
 (Continued)

(58) Field of Classification Search
 CPC ..... A61B 5/15; A61B 5/150977; A61B 5/151; A61B 5/15045; A61B 5/150458; A61B 10/02
 See application file for complete search history.

(56) References Cited

U.S. PATENT DOCUMENTS

2004/0072357 A1* 4/2004 Stiene ............... A61B 5/1473
                                                    324/449
2009/0240165 A1* 9/2009 Yoneya ............... A61B 5/151
                                                    600/583
(Continued)

FOREIGN PATENT DOCUMENTS

JP   2006-334419 A   12/2006
JP   2009-061082 A    3/2009
(Continued)

OTHER PUBLICATIONS

International Search Report PCT/ISA/210 for International Application No. PCT/JP2015/053027 dated Apr. 21, 2015.

*Primary Examiner* — Daniel L Cerioni
*Assistant Examiner* — Raymond P Dulman
(74) *Attorney, Agent, or Firm* — Harness, Dickey & Pierce, P.L.C.

(57) ABSTRACT

A medical needle comprising a flat puncturing part having front and back surfaces that are parallel to each other, wherein the puncturing part comprises a pair of side-surface inclined parts and provided at tips of respective side surfaces and a front-surface inclined part provided at a tip of the front surface, the pair of side-surface inclined parts and the front-surface inclined part each extend in an inclined manner relative to a puncturing direction so as to be tapered, and the tip of the front-surface inclined part adjoins a blade edge part formed by adjoining the tips of the pair of side-surface inclined parts and a depression is formed in the front surface of the puncturing part so as to partially indent the pair of side-surface inclined parts and the front-surface inclined part.

18 Claims, 7 Drawing Sheets

(52) U.S. Cl.
CPC .... *A61B 5/150022* (2013.01); *A61B 5/15045* (2013.01); *A61B 5/15109* (2013.01); *A61B 5/15117* (2013.01); *A61B 5/150458* (2013.01); *A61B 5/150648* (2013.01); *A61B 5/150977* (2013.01); *A61B 10/02* (2013.01)

(56) References Cited

U.S. PATENT DOCUMENTS

| | | | | |
|---|---|---|---|---|
| 2009/0318946 | A1* | 12/2009 | Tamesada | A61B 5/150022 606/181 |
| 2011/0230905 | A1* | 9/2011 | Roe | A61B 5/1411 606/181 |
| 2011/0288574 | A1* | 11/2011 | Curry | A61B 5/14546 606/185 |
| 2012/0238841 | A1* | 9/2012 | Castle | A61B 5/14532 600/316 |
| 2013/0006147 | A1* | 1/2013 | Fukuda | A61B 5/1411 600/573 |
| 2013/0103069 | A1* | 4/2013 | Roe | A61B 5/1411 606/181 |

FOREIGN PATENT DOCUMENTS

| | | |
|---|---|---|
| JP | 2010-017275 A | 1/2010 |
| JP | 2011-183076 A | 9/2011 |

\* cited by examiner (a)　　　　　　　　(b)　　　　　　　　(c)

MEDICAL NEEDLE AND PUNCTURE TOOL

CROSS-REFERENCE TO RELATED APPLICATIONS

This is a National Phase of PCT Patent Application No. PCT/JP2015/053027 filed on Feb. 4, 2015, and claims priority to Japanese Patent Application No. 2014-026564, filed Feb. 14, 2014, the contents of each of which are hereby incorporated by reference in their entirety.

TECHNICAL FIELD

The present invention relates to a medical needle for puncturing a living body and a puncture tool provided with such a medical needle.

BACKGROUND ART

To date, with respect to medical needles for puncturing a living body such as a human body, research has been made on configurations for reducing pain during puncturing. For example, the medical needle disclosed in Patent Literature 1 has ascending regions and descending regions whose cross-sectional areas increase or decrease with a predetermined regularity according to the distance from the tip. The frictional force between the needle and surrounding cells, which increases as the ascending region at the furthest tip penetrates a living body, is reduced due to the subsequent passage of the descending region, and it is thus possible to prevent damage to the surrounding cells and lessen pain.

CITATION LIST

Patent Literature

Patent Literature 1: JP 2006-334419A

SUMMARY OF INVENTION

Technical Problem

However, the above-described conventional medical needle encounters a large puncture resistance when the ascending region at the furthest tip penetrates a living body, and therefore there is still some room for further improvement in order to lessen pain that occurs immediately after puncturing.

Accordingly, an object of the present invention is to provide a medical needle and a puncture tool that can reliably puncture a living body while lessening pain inflicted on the living body during puncturing.

Solution to Problem

The aforementioned object of the present invention is achieved by a medical needle comprising a flat puncturing part having front and back surfaces that are parallel to each other, wherein the puncturing part comprises a pair of side-surface inclined parts provided at tips of respective side surfaces and a front-surface inclined part provided at a tip of the front surface, the pair of side-surface inclined parts and the front-surface inclined part each extend in an inclined manner relative to a puncturing direction so as to be tapered, and the tip of the front-surface inclined part adjoins a blade edge part formed by adjoining the tips of the pair of side-surface inclined parts, and a depression is formed in the front surface of the puncturing part so as to partially indent the pair of side-surface inclined parts and the front-surface inclined part.

In this medical needle, it is preferable that the pair of side-surface inclined parts are formed in a planar shape approximately perpendicular to the front and back surfaces of the puncturing part.

It is preferable that a through-hole that penetrates to a back surface side of the puncturing part is formed in a base surface of the depression.

It is preferable that the depression extends in the puncturing direction and is formed such that a width increases from a base surface toward the front surface.

It is preferable that the medical needle further comprises a holding part connected to a rear end side of the puncturing part, and that a flow channel that is in communication with the depression is formed on a front surface side of the holding part.

Moreover, the aforementioned object of the present invention is achieved by a puncture tool comprising the above-described medical needle and a casing accommodating the medical needle such that the medical needle is capable of advancing.

Advantageous Effects of Invention

The present invention can provide a medical needle and a puncture tool that can reliably puncture a living body while lessening pain inflicted on the living body during puncturing.

DESCRIPTION OF EMBODIMENTS

Figure 1:
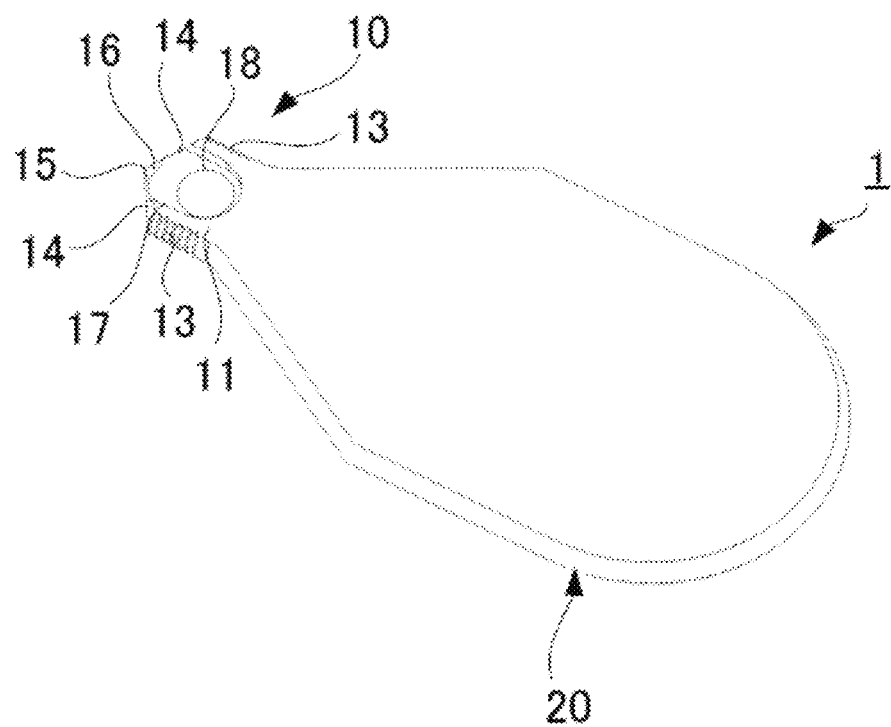
FIG. 1 is a perspective view of the front surface side of a medical needle according to one embodiment of the present invention.
Figure 2:
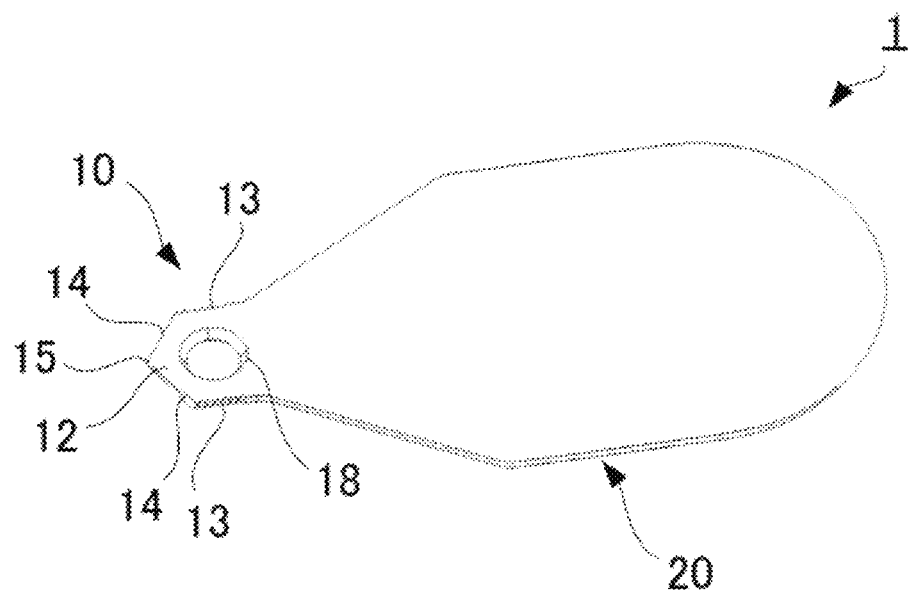
FIG. 2 is a perspective view of the back surface side of the medical needle shown in FIG. 1.

Below, embodiments of the present invention will now be described with reference to the appended drawings. FIG. 1 is a perspective view of the front surface side of a medical needle according to one embodiment of the present invention, and FIG. 2 is a perspective view of the back surface side of this medical needle. As shown in FIGS. 1 and 2, a medical needle 1 comprises a puncturing part 10 for puncturing a living body and a holding part 20 connected to the rear end side of the puncturing part 10, and is formed in a plate shape as a whole.

Figure 3:
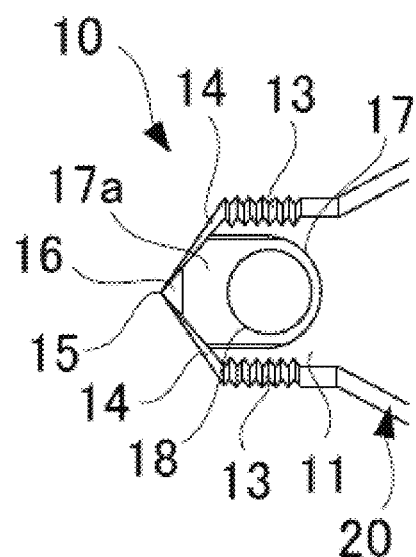
FIG. 3 is a plan view of a principal part of the medical needle shown in FIG. 1.
Figure 4:
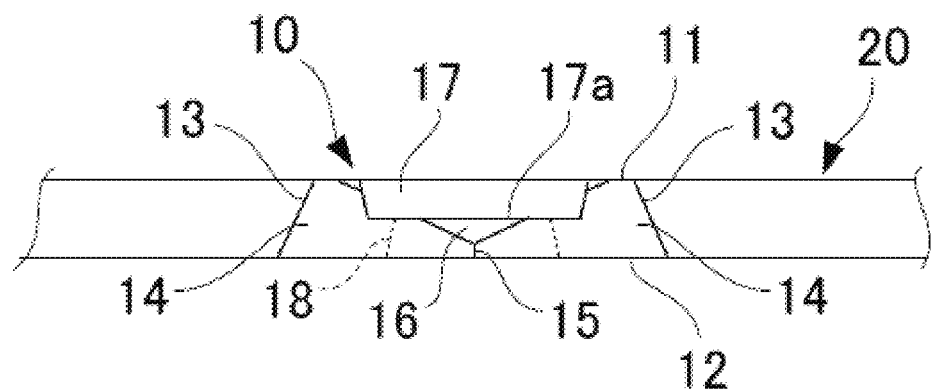
FIG. 4 is a front view of the medical needle shown in FIG. 3.

FIG. 3 is a plan view showing the puncturing part 10, which is a principal part of the medical needle shown in FIG. 1. FIG. 4 is a front view of the medical needle shown in FIG. 3. As shown in FIGS. 1 to 4, the puncturing part 10 is formed in a flat shape, the front and back surfaces are a pair of planar parts 11 and 12 that are parallel to each other, and the cross section that is perpendicular to the puncturing direction is formed in a trapezoidal shape. Other than the trapezoidal shape, examples of the cross-sectional shape of the puncturing part 10 include a rectangular shape, a polygonal shape, a shape obtained by cutting in the axial direction a circular or elliptical outer circumference so as to form planar parts that are parallel to each other, and other shapes. Sawtooth-shaped corrugations 13 and 13 that facilitate penetration of the puncturing part 10 into a living body after puncturing are formed on the respective side surfaces of the puncturing part 10.

While the width of the entire puncturing part 10 is approximately constant in the puncturing direction in this embodiment, the puncturing part 10 may be formed such that the width gradually increases toward the rear. Alternatively, the puncturing part 10 may be formed so as to become narrow (such that the width narrows) toward the rear, which is particularly suitable for an application in which it is desired to maintain the penetration of the puncturing part 10 in a living body Examples of parts of a living body that the puncturing part 10 penetrates include cells, tissues, organs, digestive tracts, blood vessels, nerves, skins, muscles, eyes, and the like.

At the tips of the respective side surfaces of the puncturing part 10, a pair of side-surface inclined parts 14 and 14 extending in an inclined manner relative to the puncturing direction are provided such that the puncturing part 10 is tapered. The pair of side-surface inclined parts 14 and 14 are formed in a planar shape approximately perpendicular to the front and back surfaces (planar parts 11 and 12) of the puncturing part 10. The tips of the pair of side-surface inclined parts 14 and 14 mutually adjoin via a linear blade edge part 15 that is perpendicular to the front and back surfaces of the puncturing part 10 as viewed from the front, and it is thus possible to secure the strength of the blade edge part 15 and reliably puncture a living body.

At the tip of the front surface (planar part 11) of the puncturing part 10, a front-surface inclined part 16 extending in an inclined manner relative to the puncturing direction is provided such that the puncturing part 10 is tapered. The front-surface inclined part 16 is formed in a planar shape, and the tip adjoins the blade edge part 15. In this embodiment, the blade edge part 15 is formed in a linear shape perpendicular to the front and back surfaces of the puncturing part 10 as viewed from the front, and the front-surface inclined part 16 adjoins one end of the blade edge part 15, but the shape of the blade edge part 15 is not particularly limited. For example, the blade edge part 15 may be configured to extend so as to be linear or curved along the front and back surfaces of the puncturing part 10 as viewed from the front so that the tip of the front-surface inclined part 16 adjoins the entire blade edge part 15. Furthermore, the tips of the pair of side-surface inclined parts 14 and 14 and the front-surface inclined part 16 may be configured to adjoin substantially at one point in the blade edge part 15.

A depression 17 is formed on the front surface side of the puncturing part 10. The depression 17 is formed so as to extend in the puncturing direction and is formed such that the tip side partially indents the pair of side-surface inclined parts 14 and 14 and the front-surface inclined part 16. The rear end side of the depression 16 is blocked by the side wall A base surface 17a of the depression 17 is formed parallel to the planar parts 11 and 12. The side wall of the depression 17 is formed in such a tapered shape that the width of the depression 17 increases from the base surface 17a toward the front surface (plane 11). It is preferable that the depression 17 is formed to span across the pair of side-surface inclined parts 14 and 14 and the front-surface inclined part 16 so as to leave the blade edge part 15. In this embodiment, as shown in FIG. 4, the depression 17 is formed such that the respective corners of the base surface 17a of the depression 17 indent the pair of side-surface inclined parts 14 and 14 and that the central part of the depression 17 indents the front-surface inclined part 16. Although it is preferable that there is only one depression 17, a plurality of depressions can also be formed so as to respectively indent the pair of side-surface inclined parts 14 and 14 and the front-surface inclined part 16.

A through-hole 18 that penetrates to the back surface side of the puncturing part 10 is formed in the base surface 17a of the depression 17. The through-hole 18 is formed in a tapered shape such that the diameter increases from the front surface (plane 11) side toward the back surface (plane 12) side. It is preferable that the puncturing part 10 has such a length that the through-hole 18 can reach the desired depth in a living body (for example, about 0.2 to 300 mm). Although there is only one through-hole 18 in this embodiment, a plurality of through-holes may be formed in the puncturing direction in the base surface 17a of the depression 17.

The holding part 20 is formed so as to be greatly enlarged from the rear end side of the puncturing part 10 such that the holding part 20 does not penetrate a living body and can support the puncturing part 10 from outside the living body. The shape and the size of the holding part 20 are not particularly limited.

When making a puncture by pressing the blade edge part 15 against the surface of a living body such as skin, the pair of side-surface inclined parts 14 and 14 and the front-surface inclined part 16 are inserted while pushing open the object to be punctured, and therefore the medical needle 1 having the above-described configuration can reliably make a puncture with the puncturing part 10 in the living body. It is preferable that the pair of side-surface inclined parts 14 and 14 are in a planar shape approximately perpendicular to the front and back surfaces (planar parts 11 and 12) of the puncturing part 10, and thereby it is possible to reliably push open the object to be punctured in the width direction to make a puncture.

Moreover, since the depression 17 is formed in the surface of the puncturing part 10 so as to partially indent the pair of side-surface inclined parts 14 and 14 and the front-surface inclined part 16, it is possible to suppress an increase in puncture resistance associated with the insertion of the puncturing part 10 and thus possible to reduce pain inflicted on a living body. As shown in the front view in FIG. 4, in this embodiment, the base surface 17a of the depression 17 traverses the front-surface inclined part 16, and the respective side edge parts extend to the pair of side-surface inclined parts 14 and 14, and thereby the puncture resistance that the pair of side-surface inclined parts 14 and 14 and the front-surface inclined part 16 encounter is reduced. With respect to the pair of side-surface inclined parts 14 and 14 and the front-surface inclined part 16 that are indented by the depression 17, portions on the periphery of the blade edge part 15 are retained to such an extent that a puncture can be reliably made, and the shape, position, size, and other features of the depression 17 are not particularly limited.

By piercing the skin of a living body, the depression 17 and the through-hole 18 can be filled with and collect an intended sample to be collected, such as blood, a body fluid, or a tissue. Alternatively, by filling the depression 17 and the through-hole 18 in advance with a substance such as a drug to be administered into a living body and making a puncture in a predetermined site of a living body; the substance can be administered in a pinpoint manner. The substance to be administered and the sample to be collected may be in various forms such as liquid, solid, semisolid (gel), freeze-dried, and nanoparticle forms. The sizes of the depression 17 and the through-hole 18 are not particularly limited, and examples include those having an inner volume of about 0.001 µl to 1 ml each.

When the depression 17 and the through-hole 18 are filled in advance with a substance to be administered, the area of the substance filled in the depression 17 and exposed to the front surface side of the puncturing part 10 is larger than the area of the substance filled in the through-hole 18 and exposed to the back surface side of the puncturing part 10. Therefore, when the puncturing part 10 penetrates a living body and receives a uniform pressure from outside, there is a difference between the forces that the substance receives from the front and back surfaces of the puncturing part 10, thus the substance filled in the depression 17 is likely to pass through the through-hole 18 and be released from the back surface side of the puncturing part 10. On the other hand, when collecting a sample to be collected into the depression 17 and the through-hole 18, the sample is likely to be drawn in from the through-hole 18 and filled in the depression 17. Thus, forming the through-hole 18 in the base surface 17*a* of the depression 17 makes it possible to easily and reliably administer a substance as well as collect a sample.

Although the width of the depression 17 and the cross-sectional area of the through-hole 18 may be constant in the thickness direction of the puncturing part 10, it is preferable to form the depression 17 and the through-hole 18 so as to be tapered such that the width and the cross-sectional area increase toward the front surface or the back surface from inside. This configuration makes it possible to increase the area of contact of the inner walls of the depression 17 and the through-hole 18 with the substance to be administered or the sample to be collected, thus facilitating the retention of the substance or the sample inside the depression 17 and the through-hole 18 and also making it easy to administer the substance or collect the sample. The effect of such an increased contact area is particularly prominent when the depression 17 and the through-hole 18 are small (for example, an inner volume of 100 nL or less).

The puncturing and the removal of the puncturing part 10 can be performed by grasping the holding part 20 with a tool or by hand. The puncturing part 10 may be removed immediately after puncturing when the purpose of puncturing is mere piercing. On the other hand, in the case of administering a drug or collecting a sample, the puncturing part 10 may be retained in a living body for a predetermined amount of time and then removed, in accordance with the kind of drug and the administration method it is thereby possible to release a precise amount of a drug into a living body; or collect only a necessary amount of a sample to perform measurement or the like.

The puncturing part 10 can be made from a biocompatible material. Examples of biocompatible materials include macromolecular polymers, biopolymers, proteins, and biocompatible inorganic materials.

Macromolecular polymers that are usable for medical applications can be preferably used, and examples include polyvinyl chloride, polyethylene glycol, parylene, polyethylene, polypropylene, silicone, polyisoprene, polymethyl methacrylate, fluororesins, polyether imide, polyethylene oxide, polyethylene terephthalate, polyethylene succinate, polybutylene terephthalate, polybutylene succinate, polybutylene succinate/carbonate, polyphenylene oxide, polyphenylene sulfide, poly-formaldehyde, polyanhydride, polyamides (nylon 6, nylon 66), polybutadiene, polyvinyl acetate, polyvinyl alcohol, polyvinylpyrrolidone, polyesteramide, poly methyl methacrylate, polyacrylonitrile, polysulfone, polyether sulfone, ABS resins, polycarbonate, polyurethanes (polyetherurethane, polyesterurethane, polyetherurethaneurea), polyvinylidene chloride, polystyrene, polyacetal, poly butadiene, ethylene-vinyl acetate copolymers, ethylene-vinyl alcohol copolymers, ethylene-propylene copolymers, polyhydroxyethyl methacrylate, polyhydrobutyrate, polyorthoester, polylactic acid, polyglycol, polycaprolactone, polylactic acid copolymers, polyglycolic acid-glycol copolymers, polycapronolactone copolymers, polydioxanone, perfluoroethylene-propylene copolymers, cyanoacrylate polymers, polybutyl cyanoacrylate, polyaryl ether ketone, epoxy resins, polyester resins, polyimide, phenolic resins, acrylic resins, and the like.

Examples of biopolymers include cellulose, starch, chitin and chitosan, agar, carrageenan, alginic acid, agarose, pullulan, mannan, curdlan, xanthane gum, gellan gum, pectin, xyloglucan, guar gum, lignin, oligosaccharide, hyaluronic acid, schizophyllan, lentinan, and the like. Examples of proteins include collagen, gelatin, keratin, fibroin, glue, sericin, vegetable proteins, milk proteins, egg proteins, synthetic proteins, heparin, nucleic acid, and the like, as well as sugar, candies, glucose, malt sugar, sucrose, maltose, monosaccharides, polysaccharides, polymer alloys thereof, and the like.

Examples of biocompatible inorganic materials include ceramics such as glass, nanocomposite ceramics, $Al_2O_3/ZrO_2$ composite ceramics, $Si_3N_4$ nanocomposite materials, hydroxyapatite, calcium carbonate, carbon, graphite (nanografibers), carbon nanotuhe (CNT), fullerene composite materials, hydroxyapatite polymer composite materials, cobalt-chromium alloys, stainless steel, titanium, titanium alloys, and the like.

Among these biocompatible materials, it is preferable to use a biodegradable material selected from biodegradable polymers including, for example, polylactic acid, polyglycolic acid, polycaprolactone, collagen, starch, hyaluronic acid, alginic acid, chitin, chitosan, cellulose or gelatin as well as compounds thereof. This is because such materials decompose in the presence of microorganisms and thus can easily be discarded after use.

It is particularly preferable to use a material selected from polylactic acid, polyglycolic acid, polycaprolactone, polydioxanone, and copolymers thereof. This is because such materials have a suitable level of affinity with biological fluids such as blood and body fluids and, therefore, such materials make it easy to accommodate a biological fluid in the depression 17 and the through-hole 18 and prevent excessive adsorption of components contained in the biological fluid.

In the case where the puncturing part 10 is made of such a biocompatible material, it is preferable that biocompatibility improving treatment is performed on the entire surface of the puncturing part 10. It is particularly preferable to perform biocompatibility improving treatment on the inner wall surface of the depression 17 and the through-hole 18. This biocompatibility improving treatment is a surface treatment performed to modify the surface that comes into contact with a biological fluid or to attach a surface treatment agent, for adjusting the affinity with the biological fluid or for making it easy to control adsorption of components contained in the biological fluid.

The biocompatibility improving treatment for adjusting the affinity with a biological fluid can be performed by coating and fixing a medium such as polyethylene glycol, sodium hydroxide, citric acid, polyoxyethylene polyoxypropylene polysorbate, Poloxamer, silicone, or the like.

Also, the biocompatibility improving treatment for malting it easy to control adsorption of components contained in a biological fluid can be performed by coating and fixing a medium such as heparin, phosphoric acid, polyethylene glycol, sodium hydroxide, citric acid, polyoxyethylene polyoxypropylene glycol, polysorbate, Poloxamer, silicone, or the like.

It is possible to evaluate the affinity with a biological fluid by the angle of contact although the evaluation is not limited to this procedure. Ensuring a suitably selected level of affinity makes it easy to accommodate the biological fluid in the depression 17 and the through-hole 18. On the other hand, it is preferable that adsorption of components of the body composition fluid is avoided as much as possible within a range in which the affinity with the body composition fluid is not impaired.

Although it is possible to fabricate the holding part 20 from a material different from the material of the puncturing part 10, it is preferable to fabricate the holding part 20 integrally with the puncturing part 10 using the same material. For example, it is possible to form the puncturing part 10 and the holding part 20 into a single body using any of the aforementioned materials by means of a molding unit including upper and lower dies.

The depression 17 and the through-hole 18 in the puncturing part 10 can be formed by injection molding using upper and lower dies each provided with the corresponding projection. Such a molding method is particularly effective when the volumes of the depression 17 and the through-hole 18 are small (for example, 100 nanoliters or less). Depending on the sizes of the depression 17 and the through-hole 18, it is possible to form the depression 17 and the through-hole 18 by microfabrication laser machining using an excimer laser or a femtosecond laser or by cutting tool machining, for example.

Figure 5:
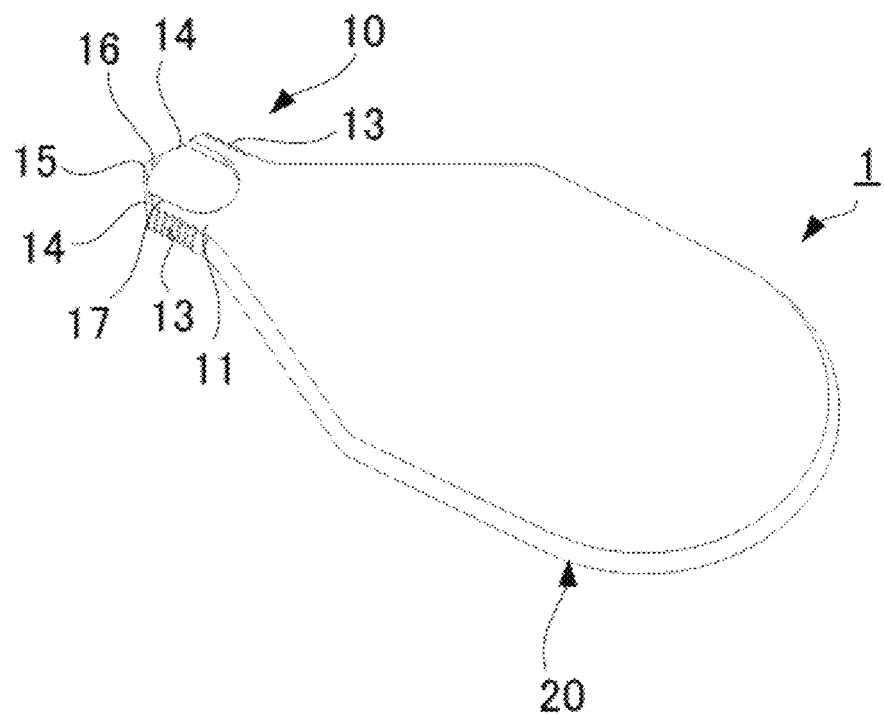
FIG. 5 is a perspective view of a medical needle according to another embodiment of the present invention.

One embodiment of the present invention has been described in detail above, but the aspects of the present invention are not limited to the above embodiment. For example, although the through-hole 18 is formed in the base surface 17a of the depression 17 in this embodiment, it is also possible to have a configuration in which there is no through-hole 18 as shown in FIG. 5. With the configuration shown in FIG. 5 as well, it is possible to reliably make a puncture in a living body while lessening pain inflicted on the living body, and it is also possible to collect a sample to be collected or administer a substance to be administered by talking advantage of the depression 17. In FIG. 5, the same components as in, for example, FIG. 1 are given the same reference numbers, and detailed descriptions thereof are omitted (the same also applies to the subsequent drawings).

Figure 6:
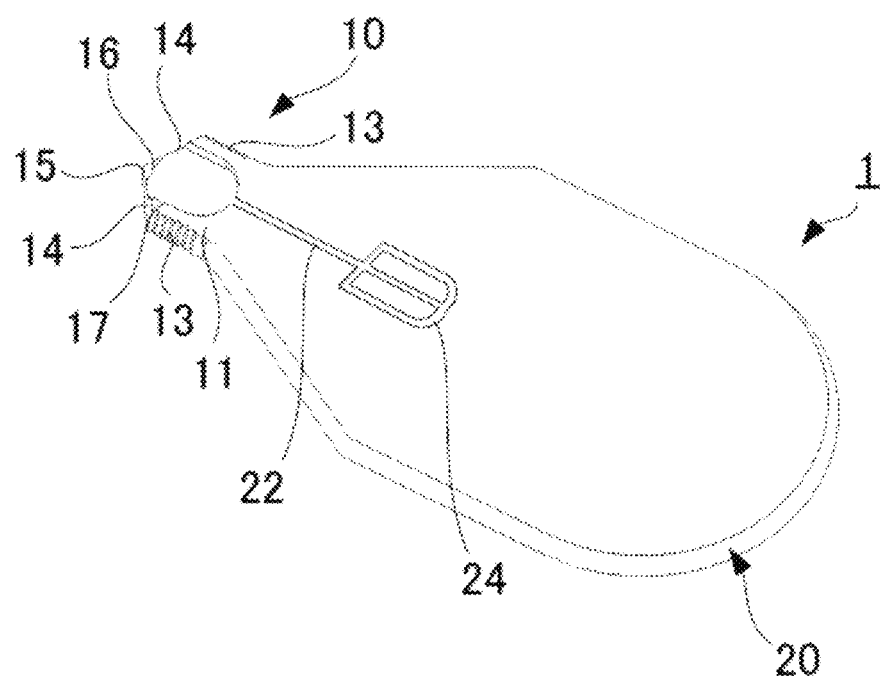
FIG. 6 is a perspective view of a medical needle according to yet another embodiment of the present invention.

Moreover, as shown in FIG. 6, forming a flow channel 22 that is in communication with the depression 17 on the front surface side of the holding part 20 makes it possible to draw, due to the capillary phenomenon, a biological fluid such as blood collected in the depression 17 by the puncturing of the puncturing part 10. The proximal end side of the flow channel 22 is in communication with a receptacle 24 formed by branching the flow channel 22, and it is thus possible to accommodate the biological fluid in the receptacle 24 to perform measurement, analysis, etc. It is possible to form the flow channel 22 so as to guide the biological fluid to the outside of the holding part 20.

Figure 7:
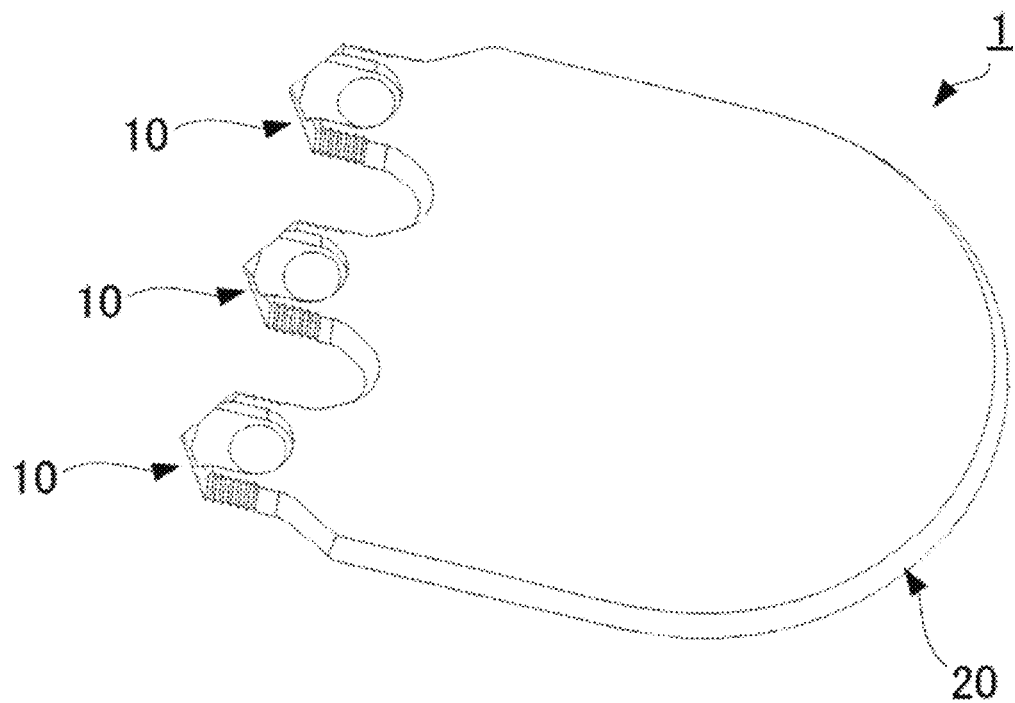
FIG. 7 is a perspective view of a medical needle according to yet another embodiment of the present invention.

Although the holding part 20 is configured to hold a single puncturing part 10 in this embodiment, it is also possible to configure the holding part 20 to hold a plurality of puncturing parts 10 as shown in FIG. 7. According to this configuration, the plurality of puncturing parts 10 can each collect a sample to be collected or administer a substance to be administered, and this configuration is thus particularly effective when the amount of the sample or the substance is large. Although all puncturing parts 10 have the same size and shape in FIG. 7, the puncturing parts 10 may have mutually different lengths in the puncturing direction, sizes of the depressions, and the like. For example, configuring each puncturing part 10 to have a different length in the puncturing direction makes it possible to administer a substance into or collect a sample from, for example, intracutaneous, subcutaneous, and intramuscular sites in a living body located at different depths. In the case of administration by the plurality of puncturing parts 10, it is possible to administer different substances by the puncturing parts 10. Moreover, it is possible to administer a substance by one puncturing part 10 and, at the same time, collect a sample by another puncturing part 10.

The medical needle 1 of each embodiment above can be used singly. Alternatively, the medical needle of the present invention can also be used as a puncture tool in which the medical needle is accommodated in a casing so as to be capable of advancing. Examples of the puncture tool include an indwelling needle system including the medical needle of any of the above-described embodiments as an inner needle disposed inside a casing (outer needle) made from a flexible material, a puncture needle cartridge removably attached to the main body of a puncture apparatus, a puncture device capable of making a puncture by itself without requiring the main body of a puncture apparatus, and the like.

Figure 8:
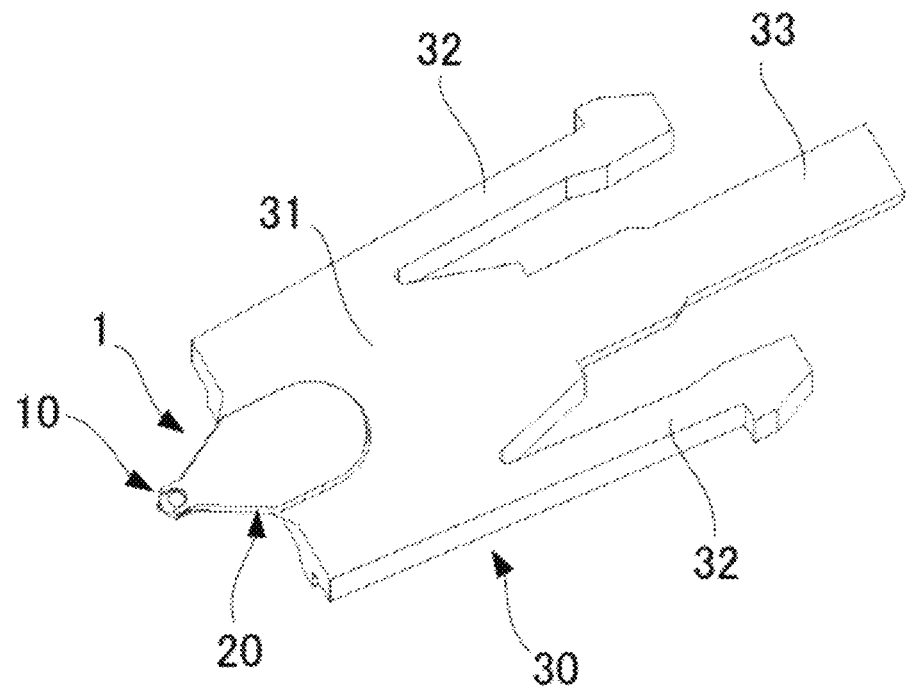
FIG. 8 is a perspective view of a medical needle according to yet another embodiment of the present invention.

FIG. 8 is a perspective view showing one example of a configuration in which the medical needle 1 shown in FIG. 1 is accommodated in a casing to be used as a puncture tool. The medical needle 1 shown in FIG. 8 is fixed to a holder 30 by integral molding or the like. The holder 30 includes a main body 31 including the medical needle 1, a pair of arms 32 and 32 provided on the respective sides of the main body 31, and a rod 33 extending toward the proximal end side of the main body 31.

Figure 9:
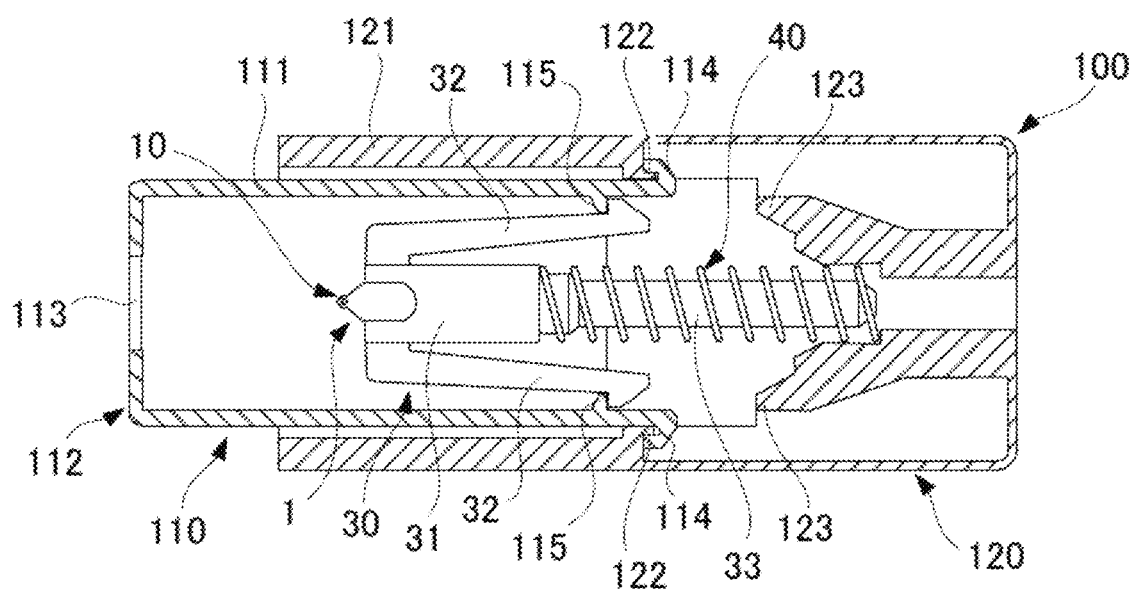
FIG. 9 is a cross-sectional view showing one example of a puncture tool including the medical needle shown in FIG. 8.

FIG. 9 is a cross-sectional view showing one example of a puncture tool including the medical needle 1 shown in FIG. 8. As shown in FIG. 9, a puncture tool 100 is configured such that the holder 30 including the medical needle 1 is accommodated so as to be capable of advancing and withdrawing in a casing composed of an inner casing 110 and an outer casing 120.

The inner casing 110 includes a contact part 112 that comes into contact with the surface of a body tissue at the tip of a main body 111, and the inner casing 110 is accommodated in the outer casing 120 such that this contact part 112 projects on the tip side of the outer casing 120. A projection opening 113 that allows the puncturing part of the medical needle 1 to project is formed in the center of the contact part 112. The rod 33 of the holder 30 is inserted into a coil spring 40.

Figure 10:
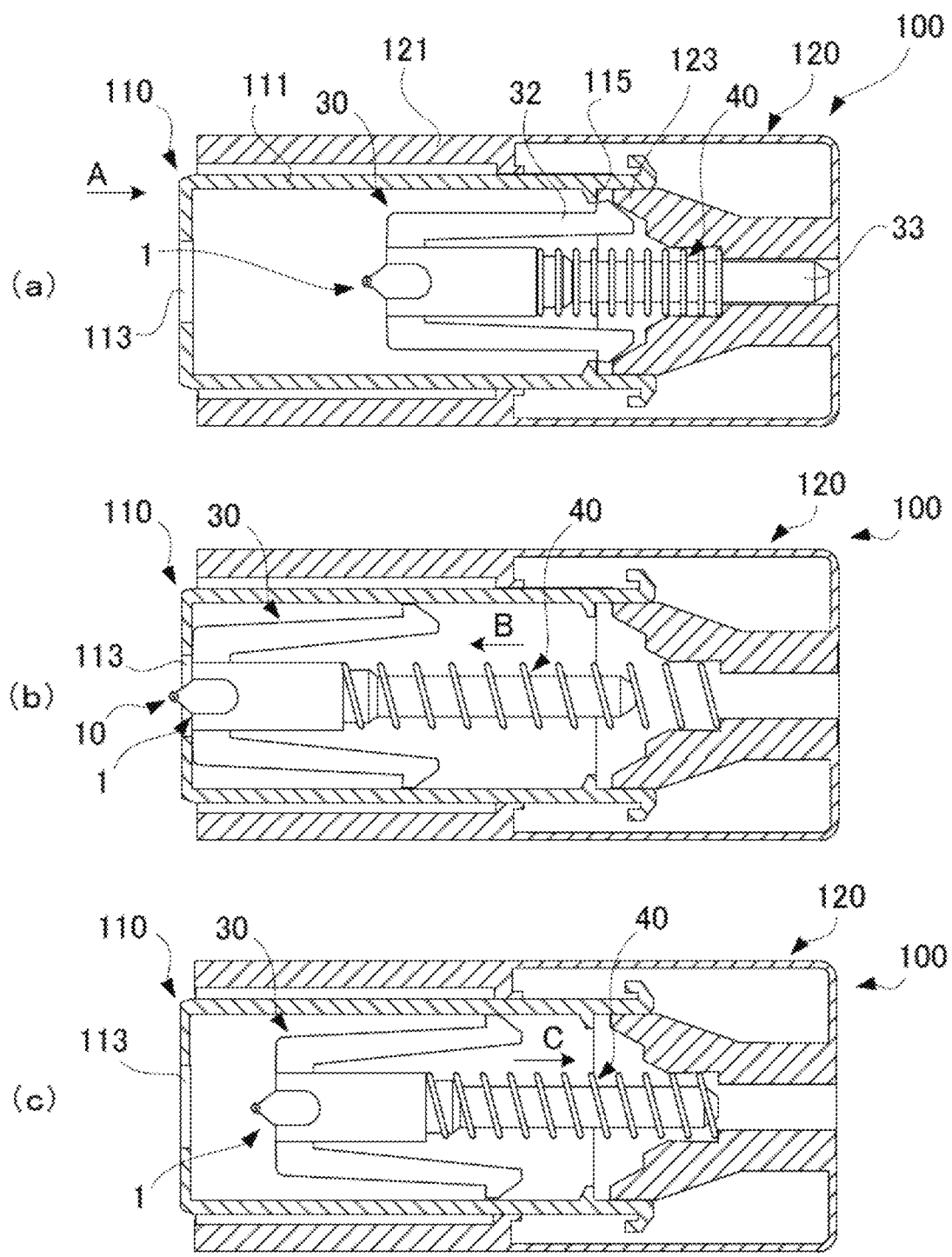
FIG. 10 shows cross-sectional views for explaining the operation of the puncture tool shown in FIG. 9.

As shown in FIG. 10(a), in the puncture tool 100 having the above-described configuration, pushing the inner casing 110 in the direction of arrow A into the outer casing 120 against the spring force of the coil spring 40 causes the inner casing 110 to move rearward together with the holder 30 and the spring force of the coil spring 40 to gradually build up. Accordingly, the rear end sides of the pair of arms 32 and 32 of the holder 30 are bent inward so as to narrow the space therebetween, thus cancelling the engagement of engagement parts 115 and the arms 32.

Once the engagement of the engagement parts 115 and the arms 32 is cancelled, the holder 30 vigorously moves in the direction of arrow B as shown in FIG. 10(b) due to the spring force built up in the coil spring 40, and the puncturing part 10 projects from the projecting opening 113 and makes a puncture. Thereafter, the length of the coil spring 40 returns to its natural length, thus the holder 30 moves in the direction of arrow C as shown in FIG. 10(c), and the medical needle 1 is accommodated inside the inner casing 110.

The puncture tool 100 described above can be used as a lancet that collects a body fluid such as blood by puncturing a body tissue at the desired depth with the medical needle 1, or can be used also in an application in which a substance to be administered such as a drug is administered into a body tissue at the desired depth. Thus, the puncture tool 100 in which the medical needle 1 can advance and withdraw in the casing (the inner casing 110 and the outer casing 120) is particularly effective when it is desired to make a puncture at a desired depth (for example, an intradermal part) for a short period of time, such as influenza vaccination. However, the puncture tool 100 is not limited to the configuration in which the medical needle 1 can advance and withdraw in the casing, and may be configured such that the medical needle advances from the casing and held at a puncturing site (or that is to say the medical needle does not withdraw after advancing from the casing).

The medical needle of the present invention can also be configured solely from the puncturing part 10 without the holding part. Since the entirety of this medical needle enters a living body, it is preferable to form the medical needle from a biodegradable material. By inserting the medical needle and keeping it in a living body, with a substance to be administered being filled in the depression 17 and the through-hole 18, it is possible to allow the medical needle 1 to decompose in the living body and promote absorption of the substance. Thus, configuring the medical needle 1 such that the entire medical needle 1 can enter a living body and be kept therein makes recovery of the injection needle unnecessary, which can solve the problem of medical wastes and is thus particularly effective in a drug delivery system (DDS).

Figure 11:
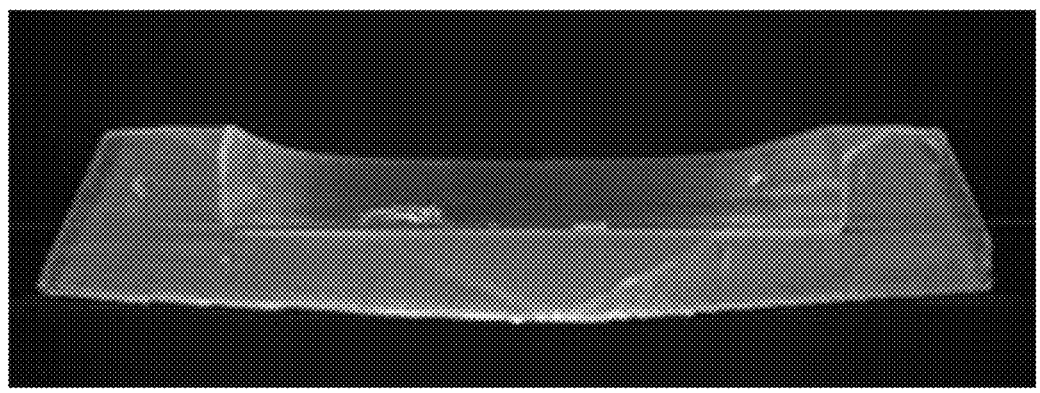
FIG. 11 is one example of an image showing the inside of a medical needle of the present invention observed with an X-ray CT scanner.
Figure 12:
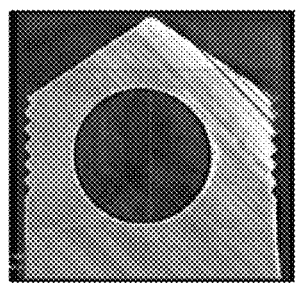
FIG. 12 shows other examples of images showing the inside of a medical needle of the present invention observed with an X-ray CT scanner.
Figure 12:
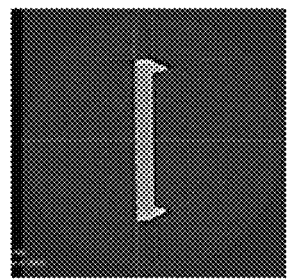
Figure 12:
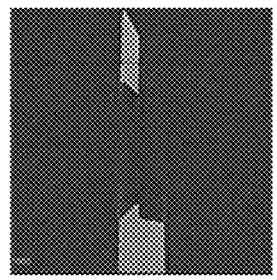

FIGS. 11 and 12 show examples of images depicting the inside of the medical needle 1 shown in FIG. 1 observed with an X-ray CT scanner (Xradia) after being formed by injection molding. It was confirmed that although the width of the puncturing part is small at no greater than 900 µm, the desired configuration of the puncturing part 10 (in particular, the shapes and the arrangements of the side-surface inclined parts, the front-surface inclined part, and the depression) is obtained.

REFERENCE SIGNS LIST

1 Medical needle
10 Puncturing part
14 Side-surface inclined part
15 Blade edge part
16 Front-surface inclined part
17 Depression
18 Through-hole
20 Holding part
100 Puncture tool
110 Inner casing
120 Outer casing

The invention claimed is:

1. A medical needle comprising:
   a flat puncturing part having a front surface and a back surface that are parallel to each other, wherein
      the flat puncturing part includes a pair of side-surface inclined parts provided at tips of respective side surfaces and a front-surface inclined part provided at a tip of the front surface of the flat puncturing part,
      the pair of side-surface inclined parts and the front-surface inclined part each extend in an inclined manner relative to a puncturing direction so as to be tapered, and the tip of the front-surface inclined part adjoins a blade edge part formed by adjoining the tips of the pair of side-surface inclined parts, and
      a depression is formed in the front surface of the flat puncturing part so as to partially indent front inclined surfaces of the pair of side-surface inclined parts and a front surface of the front-surface inclined part in a direction perpendicular to the plane of the front surface of the flat puncturing part.

2. The medical needle according to claim 1, wherein the pair of side-surface inclined parts are formed in a planar shape substantially perpendicular to the front surface and the back surface of the flat puncturing part.

3. The medical needle according to claim 1, wherein a through-hole that penetrates to a back surface side of the flat puncturing part is formed in a base surface of the depression.

4. The medical needle according to claim 1, wherein
   the depression extends in the puncturing direction; and
   a width of the depression increases from a base surface of the depression toward the front surface of the flat puncturing part.

5. The medical needle according to claim 1, further comprising:
   a holding part connected to a rear end side of the flat puncturing part; and
   a flow channel on a front surface side of the holding part, the flow channel in communication with the depression.

6. A puncture tool comprising:
   the medical needle according to claim 1, and
   a casing accommodating the medical needle such that the medical needle is capable of advancing.

7. A medical needle comprising:
   a flat puncturing part having a front surface and a back surface that are parallel to each other, wherein
      the flat puncturing part includes a pair of side-surface inclined parts provided at tips of respective side surfaces and a front-surface inclined part provided at a tip of the front surface of the flat puncturing part,
      the pair of side-surface inclined parts and the front-surface inclined part each extend in an inclined manner relative to a puncturing direction so as to be tapered, and the tip of the front-surface inclined part adjoins a blade edge part formed by adjoining the tips of the pair of side-surface inclined parts, and
      only one depression is formed in the front surface of the flat puncturing part so as to partially indent front inclined surfaces of the pair of side-surface inclined parts and a front surface of the front-surface inclined part in a direction perpendicular to the plane of the front surface of the flat puncturing part.

8. The medical needle according to claim 7, wherein the pair of side-surface inclined parts are formed in a planar shape substantially perpendicular to the front surface and the back surface of the flat puncturing part.

9. The medical needle according to claim 7, wherein a through-hole that penetrates to a back surface side of the flat puncturing part is formed in a base surface of the depression.

10. The medical needle according to claim 7, wherein
the depression extends in the puncturing direction; and
a width of the depression increases from a base surface of the depression toward the front surface of the flat puncturing part.

11. The medical needle according to claim 7, further comprising:
a holding part connected to a rear end side of the flat puncturing part; and
a flow channel on a front surface side of the holding part, the flow channel in communication with the depression.

12. A puncture tool comprising:
the medical needle according to claim 7, and
a casing accommodating the medical needle such that the medical needle is capable of advancing.

13. A medical needle comprising:
a flat puncturing part having a front surface and a back surface in parallel with one another, wherein
the flat puncturing part includes a pair of inclined side-surface parts at tips of respective side surfaces and an inclined front-surface part at a tip of the front surface of the flat puncturing part,
the pair of inclined side-surface parts and the inclined front-surface part are tapered in a puncturing direction, and the tip of the inclined front-surface part is adjacent to a blade edge part formed by adjoining the tips of the pair of inclined side-surface parts, and
front inclined surfaces of the pair of inclined side-surface parts and a front surface of the inclined front-surface part are partially indented in a direction perpendicular to the plane of the front surface of the flat puncturing part to form a depression in the front surface of the flat puncturing part.

14. The medical needle according to claim 13, wherein the pair of inclined side-surface parts have a planar shape substantially perpendicular to the front surface and the back surface of the flat puncturing part.

15. The medical needle according to claim 13, wherein a through-hole extends from a base surface of the depression to a back surface side of the flat puncturing part.

16. The medical needle according to claim 13, wherein
the depression extends in the puncturing direction; and
a width of the depression increases from a base surface of the depression toward the front surface of the flat puncturing part.

17. The medical needle according to claim 13, further comprising:
a holding part connected to a rear end side of the flat puncturing part; and
a flow channel on a front surface of the holding part, the flow channel in fluid communication with the depression.

18. A puncture tool comprising:
the medical needle according to claim 13, and
a casing configured to hold the medical needle, wherein the medical needle is configured to move within the casing.

\* \* \* \* \*